(12) United States Patent
Kohama et al.

(10) Patent No.: US 10,376,614 B2
(45) Date of Patent: Aug. 13, 2019

(54) MEDICAL DEVICE AND METHOD FOR PRODUCING THE SAME

(71) Applicant: TERUMO KABUSHIKI KAISHA, Shibuya-ku, Tokyo (JP)

(72) Inventors: Hiromasa Kohama, Kanagawa (JP); Ayako Tokue, Miyagi (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 328 days.

(21) Appl. No.: 15/058,294

(22) Filed: Mar. 2, 2016

(65) Prior Publication Data

US 2016/0175492 A1    Jun. 23, 2016

Related U.S. Application Data

(63) Continuation of application No. PCT/JP2014/069186, filed on Jul. 18, 2014.

(30) Foreign Application Priority Data

Sep. 2, 2013  (JP) ................................ 2013-181442
Jan. 28, 2014  (JP) ................................ 2014-013431

(51) Int. Cl.
*A61L 31/10* (2006.01)
*A61L 31/14* (2006.01)
*A61L 29/14* (2006.01)
*A61L 29/08* (2006.01)
*A61L 31/04* (2006.01)

(52) U.S. Cl.
CPC .............. *A61L 31/10* (2013.01); *A61L 29/085* (2013.01); *A61L 29/14* (2013.01); *A61L 31/048* (2013.01); *A61L 31/14* (2013.01); *A61L 2400/10* (2013.01); *A61L 2400/18* (2013.01)

(58) Field of Classification Search
None
See application file for complete search history.

(56) References Cited

U.S. PATENT DOCUMENTS 4,876,126 A * 10/1989 Takemura ............. A61L 29/085
                                                                        427/2.1
6,224,893 B1    5/2001 Langer et al.
2010/0303891 A1  12/2010 Lee et al.

FOREIGN PATENT DOCUMENTS

| JP | 60-259269 A | 12/1985 |
|----|---|---|
| JP | 1-033181 B2 | 7/1989 |
| JP | 2002-503230 A | 1/2002 |
| JP | 2008-279100 A | 11/2008 |
| JP | 2009-082257 A | 4/2009 |
| JP | 2010-537008 A | 12/2010 |
| JP | 2011-110393 A | 6/2011 |
| WO | WO 98/52543 A1 | 11/1998 |
| WO | WO 2009/026680 A1 | 3/2009 |

OTHER PUBLICATIONS

International Search Report (Form PCT/ISA/210) issued in PCT/JP2014/069186 dated Sep. 2, 2014.

* cited by examiner

*Primary Examiner* — Sheeba Ahmed
(74) *Attorney, Agent, or Firm* — Buchanan Ingersoll & Rooney PC

(57) ABSTRACT

A medical device and a method of manufacturing the same which excels in lubricity under severe conditions are provided. The medical device according to the present disclosure is inserted into a living body. The medical device includes a resin coating layer that includes a maleic acid polymer substance and is provided on a surface of a base member. The resin coating layer is formed by covalently bonding the maleic acid polymer substance to a reactive functional group which exists on at least the surface of the base member of the medical device. A ratio of a peak height of carboxylate with respect to a total peak height of carboxylic acid ester and a carboxylic acid in the maleic acid polymer substance ranges from 1.2 to 1.7 when being measured through infrared spectroscopy (IR method).

20 Claims, 2 Drawing Sheets

MEDICAL DEVICE AND METHOD FOR PRODUCING THE SAME

CROSS-REFERENCES TO RELATED APPLICATIONS

This application is a continuation of International Application No. PCT/JP2014/069186 filed on Jul. 18, 2014, and claims priority to Japanese Application Nos. 2013-181442 filed on Sep. 2, 2013 and 2014-013431 filed on Jan. 28, 2014, the entire content of which is incorporated herein by reference.

TECHNICAL FIELD

The present disclosure relates to a medical device and a method of manufacturing the same. For example, the present disclosure relates to a medical device and a method of manufacturing the same which excels in lubricity under severe conditions.

BACKGROUND DISCUSSION

It is desirable for a medical device such as a catheter, a guide wire, a stylet, and the like which are inserted into a body lumen such as the respiratory tract, the trachea, the alimentary canal, the urethra, a blood vessel, and the like or tissue to have operability so as not to damage the tissue and to be able to be reliably inserted into a target site. It is desirable for the medical device to exhibit excellent lubricity in order to prevent damage to mucosa caused by friction while indwelling inside tissue, or an occurrence of an inflammation.

There is a method that covalently bonds a water-soluble polymer such as a maleic anhydride polymer substance and the like to a surface of a base member of the medical device which is inserted into a living body, to thereby form a resin coating layer having lubricity (for example, refer to JP-A-S60-259269). In JP-A-S60-259269, after the coating layer of the water-soluble polymer such as a maleic anhydride polymer substance and the like is formed on the base member via a ground layer, water treatment is preferably performed, thereby exhibiting lubricity at the time of wetting.

The medical device disclosed in JP-A-S60-259269 can exhibit sufficient lubricity in normal atmosphere. However, there is a problem in that lubricity is excessively deteriorated when the medical device is under severe conditions such as high temperature, low temperature, high humidity, and the like. In recent years, during a transportation procedure when the medical device is exported or depending on an environment of a country where the medical device is used, there is the possibility that the medical device is exposed to the above-described severe conditions, for example, under an environment of high humidity.

SUMMARY

It is desirable to retain and improve the lubricity under severe conditions such as high temperature, low temperature, high humidity, and the like. Exemplary aspects of the present disclosure have been made in consideration of the above-described circumstances. An exemplary aspect is to provide a medical device and a method of manufacturing the same which excels in lubricity under severe conditions.

As a result of intensive study in order to address the above-described problem, the inventors have found that the above-described problem can be addressed by forming a coating layer including a maleic acid polymer substance in which a proportion of carboxylate is adjusted to be within a predetermined range, on a base member of a medical device.

According to an exemplary aspect, a medical device is provided which is inserted into a living body. The medical device includes a resin coating layer that includes a maleic acid polymer substance and is provided on a surface of a base member. The resin coating layer is formed by covalently bonding the maleic acid polymer substance to a reactive functional group which exists on at least the surface of the base member of the medical device. A ratio of a peak height of carboxylate with respect to a total peak height of carboxylic acid ester and a carboxylic acid in the maleic acid polymer substance ranges from 1.2 to 1.7 when being measured through infrared spectroscopy (IR method).

According to an exemplary aspect, a method of manufacturing a medical device according to the present disclosure is provided including treating a base member of the medical device, with a solution including a compound which has a reactive functional group to form a ground layer in which the reactive functional group exists, on at least a surface of the base member; and treating the base member in which the ground layer is formed, with a maleic acid polymer substance, to covalently bond the reactive functional group and the maleic acid polymer substance to each other and to form a resin coating layer which includes the maleic acid polymer substance, on the ground layer; followed by performing alkali treatment of the base member in which the ground layer and the resin coating layer are formed. The alkali treatment is performed by dipping the base member in which the ground layer and the resin coating layer are formed, in the alkaline solution of which pH is equal to or greater than 9.5 at a temperature ranging from 25° C. to 70° C. for a period ranging from 0.1 hours to 20 hours.

BRIEF DESCRIPTION OF THE DRAWINGS

In FIG. 1, the reference numeral 1 indicates water; the reference numeral 2 indicates a petri dish; the reference numeral 3 indicates a medical device (sample); the reference numeral 4 indicates a columnar butyl rubber terminal; the reference numeral 5 indicates a load; the reference numeral 6 indicates a moving table; and the reference numeral 10 indicates a friction tester.

DETAILED DESCRIPTION

The present disclosure provides a medical device which is inserted into a living body. The medical device includes a resin coating layer that includes a maleic acid polymer substance (hereinafter, will be also referred to as "a coating layer") and is provided on a surface of a base member. The resin coating layer is formed by covalently bonding the maleic acid polymer substance to a reactive functional group which exists on at least the surface of the base member of the medical device. A ratio of a peak height of carboxylate with respect to a total peak height of carboxylic acid ester and a carboxylic acid in the maleic acid polymer substance (hereinafter, will be also referred to as "a peak height ratio" or "an IR ratio") ranges from 1.2 to 1.7 when being measured through infrared spectroscopy (IR method). The coating layer including the maleic acid polymer substance in which a proportion of carboxylate is adjusted to be within the above-described predetermined range is provided (for example, formed) on the surface of the base member. With this constitution, even when being under severe conditions such as high temperature, low temperature, high humidity, and the like, for example, under an environment of high humidity, the medical device can retain and exhibit excellent lubricity without deterioration of the lubricity at the time of wetting.

Even though a mechanism providing the above-described effect is unknown, the mechanism is presumed to be as follows. The present disclosure is not limited to the below-described mechanism. When a maleic acid polymer substance comes into contact with a body fluid or blood, carboxylate (for example, an alkali metal salt in a carboxyl group) which exists in the substance swells due to a body fluid or blood and gelates, thereby exhibiting lubricity. Therefore, generally, in a maleic acid polymer substance constituting the coating layer, as the abundance of carboxylate in the maleic acid polymer substance (for example, an alkali metal salt in a carboxyl group) increases (the peak height ratio increases), swelling characteristics (lubricity) at the time of wetting are enhanced further. However, when being under severe conditions described above (for example, conditions of high humidity), a metal salt (—COOX) of a carboxyl group is transformed into a carboxyl group (—COOH), and the proportion of carboxylate (the peak height ratio) of the maleic acid polymer substance in the coating layer decreases, thereby leading to deterioration of swelling characteristics (lubricity) at the time of wetting. Therefore, as described in the present disclosure, a sufficient amount of carboxylate (a metal salt of a carboxyl group) remains in the maleic acid polymer substance by adjusting the proportion of carboxylate (the peak height ratio) so that carboxylate (a metal salt of a carboxyl group) abounds therein, even after the maleic acid polymer substance is placed under severe conditions described above (particularly, conditions of high humidity) and a portion of a metal salt of a carboxyl group is transformed into a carboxyl group (—COOX→—COOH). Therefore, even after being under severe conditions such as high temperature, low temperature, high humidity, and the like, the coating layer according to the present disclosure can retain and exhibit excellent lubricity by causing a sufficient amount of carboxylate (for example, an alkali metal salt in a carboxyl group) to swell due to a body fluid or blood and to gelate, without deterioration of the lubricity at the time of wetting. Accordingly, in the medical device according to the present disclosure, lubricity can be suppressed and prevented from deteriorating under severe conditions, and thus, it is possible to retain and exhibit excellent lubricity at the time of wetting. For this reason, the medical device according to the present disclosure can retain and exhibit excellent lubricity even when being influenced by a severe environment and the like occurring at the time of transportation or in a country where the medical device is used.

Hereinafter, exemplary embodiments of the present disclosure will be described. In this description, the expression "X to Y" indicating a range denotes "from X to Y". The terms "weight" and "mass", "weight %" and "% by mass", and "part by weight" and "part by mass" are regarded as synonyms. In addition, unless otherwise specified, operations, measurement of physical properties, and the like are performed under conditions at room temperature (20° C. to 25° C.) and relative humidity ranging from 40% to 50%.

The medical device according to the present disclosure is a medical device which is inserted into a living body. The medical device includes the resin coating layer that includes a maleic acid polymer substance and is formed on the surface of the base member (for example, a portion thereof) which is inserted into a living body. The medical device may have various uses. However, in consideration of an effect of providing lubricity when contacting with a body fluid or blood, it is exemplary that the medical device is used with being in contact with a body fluid or blood. For example, it is possible to exemplify catheters such as an indwelling needle, an IVH catheter, a thermo-dilution catheter, a blood vessel contrast catheter, a blood vessel expansion catheter (for example, a PTCA catheter), a dilator, an introducer, and the like which are inserted into or caused to indwell in a blood vessel, or a guide wire and a stylet for these catheters; catheters such as a nasogastric tube catheter, a nutritional catheter, a tube for tube-feeding nutrition (ED), and the like which are orally or nasally inserted into or caused to indwell in a digestive organ; catheters such as an oxygen catheter, an oxygen cannula, a tube or a cuff of an endotracheal tube, a tube or a cuff of a tracheotomy tube, an endotracheal suction catheter, and the like which are orally or nasally inserted into or caused to indwell in the airway or the trachea; catheters such as a urethral catheter, a catheter for guiding urine, a catheter or a balloon of a urethral balloon catheter, and the like which are inserted into or caused to indwell in the urethra or the ureter; catheters such as a suction catheter, a drainage catheter, a rectum catheter, and the like which are inserted into or are caused to indwell in various types of body cavities, internal organs, and tissues; an artificial trachea and an artificial bronchus; medical devices (an artificial lung, an artificial heart, an artificial kidney, and the like) for extracorporeal circulation treatment or circuits thereof; medical devices such as an endoscope which is inserted into various types of organs and is required to have low frictional resistance with respect to the outer surface and the like of a living body when being inserted into, being caused to slide into, and being caused to indwell in the living body, for example; and the like. Among those above, in terms of a high demand with respect to the effect of providing lubricity when contacting with a body fluid or blood, it is exemplary that the coating layer according to the present disclosure is provided on a body fluid/blood contact surface of a catheter, a guide wire, and an indwelling needle which are used inside a body lumen such as a blood vessel, the ureter, and the like.

The resin coating layer (coating layer) according to the present disclosure exhibits surface lubricity in aqueous liquid such as a body fluid, blood, a saline, and the like so that medical devices such as a catheter, a guide wire, and the like are easily inserted into a body lumen, for example, and thus, it is possible to improve the operability thereof. In addition, the resin coating layer (coating layer) according to the present disclosure can reduce damage to tissue mucosa occurring during the above-described operation.

The above-described resin coating layer is formed by covalently bonding a maleic acid polymer substance to the reactive functional group which exists on at least the surface of the base member of the medical device. In the medical devices which are intended to be used as a catheter, a guide wire, an indwelling needle, and the like, the whole surface (the surface in its entirety) of the medical device (for example, the base member) does not necessarily have lubricity. In an exemplary embodiment, the coating layer is formed on at least a surface portion of the medical device which contacts with a body fluid or blood. The coating layer can be formed on only a part of the surface portion of the medical device or can be formed on the entire surface portion of the medical device. Therefore, the present disclosure includes a case where only a portion of the surface of the base member of the medical device has lubricity and a case where the inside of the base member thereof has lubricity. In addition, the maleic acid polymer substance can exhibit high lubricity at the time of wetting and sustainability thereof.

In the above-described resin coating layer, the maleic acid polymer substance has the ratio of the peak height of carboxylate with respect to the total peak height of carboxylic acid ester and a carboxylic acid when being measured through infrared spectroscopy (IR method) (also referred to as "peak height ratio" or "IR ratio") ranging from 1.2 to 1.7. Such ratio is calculated from the following equation: (peak height of carboxylate)/(total peak height of carboxylic acid ester and carboxylic acid). If the peak height ratio is less than 1.2, it is possible to exhibit and retain excellent lubricity at the time of wetting under a normal air atmosphere, for example, under conditions at room temperature (20° C. to 25° C.) and 40% to 50% of relative humidity, which hereinafter are referred to as "normal conditions." However, the amount (the proportion) of carboxylate in the maleic acid polymer substance decreases under severe conditions such as high temperature, low temperature, high humidity, and the like, and thus, it is not possible to exhibit sufficient lubricity. On the contrary, if the peak height ratio exceeds 1.7, carboxylate excessively abounds in the coating layer so that a portion of the coating layer is dissolved when performing alkali treatment for the coating layer which is formed from the maleic acid polymer substance for the purpose of adjusting the peak height ratio, and thus, it is not possible to form the coating layer. In consideration of the degree of swelling characteristics (for example, lubricity) at the time of wetting under severe conditions and a further improved effect of retainability (for example, durability) of the effect thereof, it is exemplary that the peak height ratio ranges from 1.2 to 1.6, and it is exemplary to range from 1.2 to 1.5.

In this description, the expression "the ratio of the peak height of carboxylate (the peak height ratio or the IR ratio) with respect to the total peak height of carboxylic acid ester and a carboxylic acid when being measured through infrared spectroscopy (IR method)" regarding the maleic acid polymer substance denotes a value which is calculated by the below-described infrared spectroscopy (infrared spectroscopy; IR method) as the ratio of the peak height of carboxylate with respect to the total peak height of carboxylic acid ester and a carboxylic acid [=(peak height of carboxylate)/ (total peak height of carboxylic acid ester and carboxylic acid)]. The resin coating layer of the medical device is measured by the attenuated total reflection method (also referred to as the "ATR method") while being in a dry state. Absorbance A (in the vicinity of 1710 $cm^{-1}$ (kayser)) of carboxylic acid ester and a carboxylic acid, and absorbance B (in the vicinity of 1570 $cm^{-1}$ (kayser)) of carboxylate are individually measured while having a base line (1800 $cm^{-1}$ (kayser)) as a reference. Using the absorbance A and B, the peak height ratio (the IR ratio) is calculated by the following expression:

Peak height ratio of carboxylate with respect to total peak height of carboxylic acid ester and carboxylic acid=(absorbance $B$)/(absorbance $A$)

The maleic acid polymer substance used to form the resin coating layer may have any structure such as a homopolymer, a copolymer constituted by the above-described constituting unit and a constituting unit derived from a different monomer, and the like, for example, as long as a constituting unit derived from a maleic acid, a salt thereof, or ester thereof is included. It is exemplary that the constituting unit derived from a maleic acid, a salt thereof, or ester thereof is a constituting unit illustrated in the below-described Chemical Formulae (a), (a') and/or (a").

[Chemical Formula 1]

In the above-described Chemical Formulae, X represents an alkali metal or an alkali earth metal. As the alkali metal, for example, there are lithium, sodium, potassium, rubidium, and cesium. As the alkali earth metal, for example, there are magnesium, calcium, strontium, and barium. It is exemplary that X is sodium, potassium, magnesium, and calcium; it is exemplary to be sodium and calcium; and it is exemplary to be sodium. In a case where X is sodium, when the maleic acid polymer substance comes into contact with a body fluid or blood, a sodium salt of a carboxyl group in the maleic acid polymer substance is caused to easily swell due to a body fluid or blood and is gelated, and thus, it is possible to exhibit particularly excellent lubricity. In addition, R is a straight chain or branched alkyl group of carbon atom numbers 1 to 24. As the alkyl group, it is possible to exemplify a methyl group, an ethyl group, a propyl group, an isopropyl group, a butyl group, an isobutyl group, a sec-butyl group, a tert-butyl group, a pentyl group, an isopentyl group, a tert-pentyl group, a neopentyl group, a hexyl group, an isohexyl group, a heptyl group, an octyl group, a nonyl group, a decyl group, an undecyl group, a dodecyl group, a 2-ethylhexyl group, a tridecyl group, a tetra decyl group, a pentadecyl group, a hexadecyl group, a heptadecyl group, an octadecyl group, a nonadecyl group, an eicosyl group, an heneicosyl group, a docosyl group, and the like. Among those above, in consideration of the degree of swelling characteristics (lubricity) at the time of wetting, retainability (durability) of the effect thereof, and the like, it is exemplary that R is a straight chain or branched alkyl group of carbon atom numbers 1 to 8, it is exemplary to be a straight chain or branched alkyl group of carbon atom numbers 1 to 3. In each of the above-described constituting units, one type of constituent may exist independently, or two types or more constituents may exist in a mixed form.

Among the above-described constituting units, it is exemplary that the maleic acid polymer substance has a constituting unit of Chemical Formula (a') and/or a constituting unit of Chemical Formula (a"), and it is exemplary to have a constituting unit of Chemical Formula (a') and a constituting unit of Chemical Formula (a"). For example, the above-described composition of the constituting unit of Chemical Formula (a), the constituting unit of Chemical Formula (a'), and the constituting unit of Chemical Formula (a") is acceptable as long as the composition has the peak height ratio of the maleic acid polymer substance ranging from 1.2 to 1.7. The composition is suitably determined in accordance with the peak height ratio.

For example, a different monomer which can be copolymerized with a constituting unit derived from a maleic acid, a salt thereof, or ester thereof is not particularly limited as long as the monomer does not hinder the effect of the present disclosure (for example, lubricity at the time of wetting under normal conditions, lubricity at the time of wetting under severe conditions, and retainability of the lubricity thereof). For example, it is possible to exemplify alkyl vinyl ether; acrylamide or a derivative thereof; vinylpyrrolidone; acrylic acid, methacrylic acid, and derivatives thereof; a dienic compound; and a monomer which has maleic anhydride, a salt thereof, sugar, and phospholipid in the side chain. For example, it is possible to exemplify methyl vinyl ether, ethyl vinyl ether, propyl vinyl ether, acrylic acid, methacrylic acid, N-methyl acrylamide, N,N-dimethyl acrylamide, acrylamide, acryloyl morpholine, N,N-dimethylaminoethyl acrylate, vinylpyrrolidone, 2-methacryloyloxyethyl phosphorylcholine, 2-methacryloyloxyethyl-D-glycoside, 2-methacryloyloxyethyl-D-mannoside, vinyl methyl ether, hydroxyethyl methacrylate, and the like. Among those above, in consideration of lubricity at the time of wetting, lubricity at the time of wetting under severe conditions, retainability of the lubricity thereof, and the like, it is exemplary that the monomer is alkyl vinyl ether, and it is exemplary to be methyl vinyl ether and ethyl vinyl ether. It is exemplary that the maleic acid polymer substance is an alkyl vinyl ether-maleic acid ester copolymer, and it is exemplary to be an alkyl vinyl ether-maleic acid ester copolymer constituted by a constituting unit derived from maleic acid ester illustrated in the above-described Chemical Formula (a') and/or (a") (for example, the above-described Chemical Formulae (a') and (a")), and a constituting unit derived from alkyl vinyl ether illustrated in the below-described Chemical Formula (b).

[Chemical Formula 2]

(b)

In the above-described Chemical Formula (b), the substituted group R' in a constituting unit derived from alkyl vinyl ether is a straight chain or branched alkyl group of carbon atom numbers 1 to 24. Here, since "the alkyl group" is defined to be similar to an alkyl group related to a substituted group R in the above-described constituting unit derived from maleic acid ester, description thereof will be omitted herein. Among those above, it is exemplary that R' is a straight chain or branched alkyl group of carbon atom numbers 1 to 8, and it is exemplary to be a straight chain or branched alkyl group of carbon atom numbers 1 to 3. When the maleic acid polymer substance is a copolymer, each constituting unit may be in a block state or a random state.

In addition, when the maleic acid polymer substance is a copolymer, the composition of each constituting unit (a monomer forming each constituting unit) is not particularly limited. The composition is suitably selected in consideration of a desired effect (for example, lubricity at the time of wetting under normal conditions, lubricity at the time of wetting under severe conditions, and retainability of the lubricity thereof). For example, it is exemplary that the maleic acid polymer substance is constituted by a constituting unit derived from a maleic acid, a salt thereof, or ester thereof ranging from 20 mol % to 80 mol %, and a constituting unit derived from a different monomer ranging from 80 mol % to 20 mol %. It is exemplary to be constituted by a constituting unit derived from a maleic acid, a salt thereof, or ester thereof ranging from 30 mol % to 70 mol %, and a constituting unit derived from a different monomer ranging from 70 mol % to 30 mol %. The total amount of the constituting unit derived from a maleic acid, a salt thereof, or ester thereof, and a constituting unit derived from a different monomer is 100 mol %. For example, it is exemplary that the maleic acid polymer substance is an alkyl vinyl ether-maleic acid ester copolymer constituted by a constituting unit derived from alkyl vinyl ether ranging from 40 mol % to 60 mol % and a constituting unit derived from maleic acid ester ranging from 60 mol % to 40 mol % (the total amount of a constituting unit derived from alkyl vinyl ether and a constituting unit derived from maleic acid ester is 100 mol %).

For example, the maleic acid polymer substance may have an insolubilizing form as long as the maleic acid polymer substance has the degree of freedom in the molecular chain and can take a water-containing form. The insolubilizing form is not particularly limited; for example, the maleic acid polymer substance has the degree of freedom in the molecular chain and can take a water-containing form. For example, it is possible to exemplify a crosslinking substance and the like of a substance which has two or more reactive functional groups, and a maleic acid polymer substance. The reactive functional group includes an amidated compound, an anhydride compound, a halide, an etherified compound, a hydrolyzate, an acetal compound, a formal compound, an alkylol compound, a quaternary compound, a diazo compound, a hydrazide compound, a sulfonated compound, a nitrogenous compound, and an ion complex which can be obtained through condensation, addition, substitution, oxidation, reduction reaction, and the like of the above-described maleic acid polymer substance; and a diazonium group, an azide group, an isocyanate group, an acid chloride group, an acid anhydride group, an imino carbonate ester group, an amino group, a carboxyl group, an epoxy group, a hydroxyl group, an aldehyde group, and the like. When such a maleic acid polymer substance comes into contact with a body fluid or blood, frictional resistance with respect to a body lumen or tissues can be remarkably reduced, and thus, the maleic acid polymer substance can be used as a lubricant. In addition, a derivative which can be obtained through condensation, addition reaction, substitution reaction, and the like of the maleic acid polymer substances; and a substance which is partially crosslinked or the like is similarly effective as a lubricant.

The molecular weight of the maleic acid polymer substance is not particularly limited as well. In consideration of a desired effect (for example, lubricity at the time of wetting under normal conditions, lubricity at the time of wetting under severe conditions, and retainability of the lubricity thereof), the molecular weight thereof is suitably selected. For example, it is exemplary that the weight-average molecular weight of the maleic acid polymer substance ranges from 10,000 to 7,000,000, and it is exemplary to range from 100,000 to 5,000,000. In this description, the molecular weight (the weight-average molecular weight) of the maleic acid polymer substance is measured through gel permeation chromatography (GPC) using polystyrene as a reference substance and tetrahydrofuran (THF) as a moving phase. The molecular weight of the maleic acid polymer substance can also be calculated based on the type of the repeating unit and the number of the repeating units.

The above-described maleic acid polymer substance is covalently bonded to the reactive functional group which exists on at least the surface of the base member, thereby forming the coating layer on the base member. The coating layer can exhibit sustainable lubricity without dissolving in aqueous liquid such as a body fluid, blood, and the like. For example, the reactive functional group may be acceptable as long as the reactive functional group exists on at least the surface of the base member. The reactive functional group can be easily bonded to the maleic acid polymer substance in the coating layer. The reactive functional group may exist inside the base member in addition to the surface of the base member.

The reactive functional group is not particularly limited; for example, the reactive functional group reacts to the maleic acid polymer substance and forms a covalent bond. For example, it is possible to exemplify a diazonium group, an azide group, an isocyanate group, an acid chloride group, an acid anhydride group, an imino carbonate ester group, an amino group, a carboxyl group, an epoxy group, a hydroxyl group, a peroxide group, an aldehyde group, and the like. Among those above, it is exemplary that the reactive functional group is an isocyanate group, an amino group, an aldehyde group, or an epoxy group. Regarding the above-described reactive functional group, one type thereof may be independently used, or two types or more thereof may be used together.

The introduction form of the reactive functional group is not particularly limited. For example, any of the following forms may be used such as (i) a form of using the base member having the reactive functional group on at least the surface thereof (the base member containing the reactive functional group); (ii) a form of using the base member having the reactive functional group to be introduced to at least the surface thereof in advance; (iii) a form of forming another layer (a ground layer) having the reactive functional group on the base member; and the like. Among those above, in consideration of the degree of freedom in selecting the base member, and the like, it is exemplary to use the form of (iii). In the above-described form of (iii), it is exemplary that the base member constituting the medical device is treated with a solution of a compound which has the reactive functional group, thereby forming a ground layer in which the reactive functional group exists on at least the surface of the base member.

In the above-described form of (i), a base member which is formed from polyurethane, polyamide, and the like can be used as the base member containing the reactive functional group. In addition, in the above-described form of (ii), a method of irradiating the surface of the base member with ionization gas plasma can be used. Irradiation of ionization gas plasma may be performed under any condition. However, it is exemplary to perform irradiation with ionized gas plasma which contains oxygen or nitrogen. For example, the surface of the base member is reformed and activated by irradiating the surface of the base member with ionized gas plasma which contains oxygen, and thus, a functional group such as a carboxyl group, a hydroxyl group, a peroxide group, and the like is introduced to the surface of the base member. In the above-described method, the content of oxygen in the ionized gas is not particularly limited; for example, the content meets an amount which can provide the above-described effect. In addition, as the surface of the base member is irradiated with ionized gas plasma containing nitrogen, the surface of the base member is reformed and activated so that a functional group such as a carboxyl group, a hydroxyl group, a peroxide group, an amino group, and the like is introduced to the surface of the base member. In the above-described method, the content of nitrogen in ionized gas is not particularly limited; for example, the content meets an amount which can provide the above-described effect.

The above-described form of (iii) can be applied to a case where a base member which contains no reactive functional group is used as the base member configuring the outer wall, the inner wall, and the like of various types of the medical devices. For example, treatment is performed with a compound which has the reactive functional group, and the reactive functional group is caused to exist in the base member, thereby covalently bonding the maleic acid polymer substance to the surface thereof.

A compound which has the above-described reactive functional group is not particularly limited; for example, the compound has the above-described reactive functional group. For example, as the compound which has an isocyanate group as the reactive functional group, it is possible to exemplify ethylene diisocyanate, hexamethylene diisocyanate, xylene diisocyanate, toluene diisocyanate, tolylene diisocyanate, 4,4'-diphenylmethane diisocyanate (MDI), naphthalene diisocyanate, diphenylmethane diisocyanate, phenylene diisocyanate, cyclohexylene diisocyanate, triphenylmethane triisocyanate, polyisocyanate such as toluene triisocyanate and the like; and an adduct of the polyisocyanate and polyol (for example, trimethylol propan); a prepolymer; and the like.

As the compound which has an amino group as the reactive functional group, it is possible to exemplify low molecular polyamine such as ethylene diamine, trimethylene diamine, 1,2-diaminopropane, tetramethylene diamine, 1,3-diaminobutane, 2,3-diaminobutane, pentamethylene diamine, 2,4-diaminopentane, hexamethylene diamine, octamethylene diamine, nonamethylene diamine, decamethylene diamine, undecamethylene diamine, dodecamethylene diamine, tridecamethylene diamine, octadecamethylene diamine, N,N-dimethylethylene diamine, N,N-diethyl trimethylene diamine, N,N-dimethyl trimethylene diamine, N,N-dibutyl trimethylene diamine, N,N,N'-triethyl ethylene diamine, N-methyltrimethylene diamine, N—N-dimethyl-p-phenylene diamine, N,N-dimethyl hexamethylene diamine, diethylene triamine, triethylene tetramine, tetraethylene pentamine, heptaethylene octamine, nonaethylene decamine, 1,3-bis (2'-aminoethyl amino) propane, bis (3-amino propal) amine, 1,3-bis (3'-aminopropyl amino) propane, 1,2,3-triaminopropane, tris (2-aminoethyl) amine, tetra (aminomethyl) methane, methyl iminobispropyl amine, methyl iminobisethyl amine, ethyl iminobisethyl amine, N-aminopropyl-2-morpholine, N-aminopropyl-2-pipecholine, N-(2-hydroxyethyl) trimethylene diamine, xylylene diamine, phenylene diamine, piperazine, N-methylpiperazine, N-(2-aminoethyl) ethanol amine, N-aminoethyl piperazine, N,N,N'N'-tetramethyl ethylene diamine, N,N,N'N'-tetramethyl tetramethylene diamine, and the like; poly which is synthesized from amine, alkylene dihalide, or epichlorohydrin (alkylene polyamine) [Encyclopedia of Polymer Science and Technology, Vol. 10, page 616]; an alkyleneimine polymer which can be obtained through ring-opening polymerization of alkyleneimine such as ethyleneimine, propyleneimine, and the like [Encyclopedia of Polymer Science and Technology, Vol. 1, page 734]; and polyamine and the like such as polymer polyamine and the like such as polyvinyl amine, polylysine, and the like.

As the compound which has an aldehyde group as the reactive functional group, it is possible to exemplify polyaldehyde and the like such as glutaraldehyde, terephthalaldehyde, isophthalaldehyde, dialdehyde, starch, glyoxal, malonaldehyde, succinic acid aldehyde, adipaldehyde, pimelin dialdehyde, suberic dialdehyde, maleic aldehyde, 2-pentene-1, 5-dialdehyde, and the like.

As the compound which has an epoxy group as the reactive functional group, it is possible to exemplify polyepoxide and the like such as ethylene glycol diglycidyl ether, polyethylene glycol diglycidyl ether, propylene glycol diglycidyl ether, polypropylene diglycidyl ether, hexanediol diglycidyl ether, trimethylolpropane triglycidyl ether, and the like.

Among those above, in consideration of bonding characteristics with respect to the maleic acid polymer substance (that is, lubricity at the time of wetting under normal conditions, lubricity at the time of wetting under severe conditions, and retainability of the lubricity thereof), and the like, it is exemplary to use 4,4'-diphenyl methane diisocyanate (MDI), an adduct of tolylene diisocyanate and trimethylol propane, an adduct of hexamethylene diisocyanate and trimethylol propane, a trimmer thereof, and diethylene triamine. Regarding the compound which has the above-described reactive functional group, one type thereof may be independently used, or two types or more thereof may be used in a mixed form.

The base member used in the present embodiment may be constituted by any material. The material is not particularly limited, and the material can be suitably selected depending on the type of the medical device in which a coating layer is provided on the surface thereof. For example, as the material constituting or forming the base member, a metal material, a polymer material, glass, ceramic, and the like can be exemplified. The base member in its entirety (all) may be constituted by or formed from any one of the above-described materials, or the base member may have a structure in which the surface layer of the base member is constituted or formed by coating the surface of a core portion of the base member which is constituted by or formed from any one of the above-described materials, with another one of the above-described materials through an appropriate method. As an example of the latter case, it is possible to exemplify a base member in which the surface layer of the base member is formed by coating the surface of the core portion of the base member formed from a resin material and the like, with a metal material through an appropriate method (for example, a method in the related art such as plating, metal deposition, sputtering, and the like); a base member in which the surface layer of the base member is formed by coating the surface of the core portion of the base member formed from a hard reinforcing material such as a metal material, a ceramic material, and the like, with a polymer material softer than the reinforcing material such as a metal material and the like through an appropriate method (for example, a method in the related art such as dipping, spraying, applying and printing, and the like) or by performing complexation (appropriate reaction processing) of a reinforcing material of the core portion of the base member and a polymer material of the surface layer of the base member; and the like. Accordingly, the core portion of the base member may be a multilayered structure in which materials different from each other are stacked to form a multilayer, a structure (for example, a complex) in which each portion of the medical device is connected to a member formed from a different material, and the like. In addition, a middle layer may be additionally and separately formed between the core portion of the base member and the surface layer of the base member. In this case, a compound which has the above-described reactive functional group may be included in the surface layer of the base member. The surface layer of the base member may also be a multilayered structure in which materials different from each other are stacked to form a multilayer, a structure (for example, a complex) in which each portion of the medical device is connected to a member formed from a different material, and the like.

Among the materials constituting or forming the above-described base member, the metal material is not particularly limited. A metal material which is generally used in the medical device such as a catheter, a guide wire, an indwelling needle, and the like is used. For example, it is possible to exemplify various types of stainless steel (SUS) such as SUS304, SUS316, SUS316L, SUS420J2, SUS630, and the like; gold; platinum; silver; copper; nickel; cobalt; titanium; iron; aluminum; tin; various types of alloys such as a nickel-titanium (Ni—Ti) alloy, a nickel-cobalt (Ni—Co) alloy, a cobalt-chrome (Co—Cr) alloy, a zinc-tungsten (Zn—W) alloy, and the like; and the like. One type thereof may be independently used, or two types or more thereof may be used together. As the above-described metal material, an optimal metal material may be suitably selected for the base member intended to be used as a catheter, a guide wire, an indwelling needle, and the like.

In addition, among the materials constituting or forming the above-described base member, the polymer material is not particularly limited. A polymer material which is generally used in the medical device such as a catheter, a guide wire, an indwelling needle, and the like is used. For example, it is possible to exemplify a polyamide resin; linear low-density polyethylene (LLDPE); low-density polyethylene (LDPE); a polyethylene resin such as high-density polyethylene (HDPE) and the like, or a polyolefin resin such as a polypropylene resin and the like; a modified polyolefin resin; an epoxy resin; a urethane resin (polyurethane); a diallyl phthalate resin (an allyl resin); a polycarbonate resin; a fluorine resin; an amino resin (a urea resin, a melamine resin, a benzoguanamine resin); a polyester resin; a styrol resin; a polyacetal resin; a vinyl acetate resin; a phenol resin; a vinyl chloride resin (polyvinyl chloride); a silicone resin (a silicon resin); a polyether resin; a polyimide resin; polystyrene; polyacrylic acid ester; polymethacrylic acid ester; polyacrylonitrile; polyacrylamide; polyacrylic acid; polymethacrylic acid; polyvinyl alcohol; polymaleic anhydride; polyethylenimine; and the like. One type thereof may be independently used, or two types or more thereof may be used together. As the above-described polymer material, an optimal polymer material may be suitably selected for the base member intended to be used as a catheter, a guide wire, an indwelling needle, and the like.

In addition, the shape of the above-described base member is not particularly limited. The shape thereof is suitably selected depending on a usage form, for example, a sheet shape, a line shape (wire), a tube shape, and the like.

In an exemplary medical device according to the present disclosure, a coating layer for applying lubricity to the surface of the base member is provided so that a method of manufacturing the medical device is not particularly limited. For example, it is exemplary that the medical device according to the present disclosure is manufactured by introducing the reactive functional group to the surface of the base member, and then, treating with a maleic acid polymer substance. The reactive functional group and the maleic acid polymer substance are covalently bonded to each other, and a coating layer is formed. Thereafter, the proportion of carboxylate in the maleic acid polymer substance is adjusted so as to cause the peak height ratio to range from 1.2 to 1.7. As described above, it is exemplary that the reactive functional group is introduced to the surface of the base member by separately forming a layer (the ground layer) having the reactive functional group on the base member. It is exemplary to be introduced to the surface of the base member by treating the base member of the medical device with a solution including a compound which has the reactive functional group, and forming the ground layer in which the reactive functional group exists on at least the surface of the base member. In addition, it is exemplary that the coating layer including the maleic acid polymer substance is formed on the ground layer by treating the base member having the above-described ground layer with the maleic acid polymer substance to covalently bond the reactive functional group and the maleic acid polymer substance to each other. It is exemplary that the ratio of carboxylate (the peak height ratio) in the maleic acid polymer substance is adjusted by performing alkali treatment of the coating layer which has been formed in the above-described manner. The conditions of alkali treatment are not particularly limited; for example, the peak height ratio (the proportion of carboxylate) in the maleic acid polymer substance ranges from 1.2 to 1.7 under the conditions thereof. For example, it is exemplary to cause the base member in which the ground layer and the resin coating layer are formed to be dipped in an alkaline solution of which pH is equal to or greater than 9.5 at a temperature ranging from 25° C. to 70° C. for a period ranging from 0.1 hours to 20 hours.

It is exemplary that the medical device according to the present disclosure is manufactured by treating a base member of the medical device, with a solution including a compound which has a reactive functional group, and forming a ground layer in which the reactive functional group exists, on at least a surface of the base member [Step (1)]; and treating the base member in which the ground layer is formed, with a maleic acid polymer substance, to covalently bond the reactive functional group and the maleic acid polymer substance to each other and to form a resin coating layer which includes the maleic acid polymer substance, on the ground layer [Step (2)]; followed by performing alkali treatment of the base member in which the ground layer and the resin coating layer are formed [Step (3)].

It is exemplary that the alkali treatment is performed by dipping the base member in which the ground layer and the resin coating layer are formed, in the alkaline solution of which pH is equal to or greater than 9.5 at a temperature ranging from 25° C. to 70° C. for a period ranging from 0.1 hours to 20 hours. Hereinafter, a favorable method of manufacturing the above-described medical device according to the present disclosure will be described in detail. It should be noted that the present disclosure is not limited to the below-described form.

1. Step (1)

In this Step, the base member of the medical device is treated with a solution (an applying solution) including a compound which has a reactive functional group, thereby forming a ground layer in which a reactive functional group exists, on at least the surface of the base member.

The method of treating the base member of the medical device (also referred to as "the base member") with a solution including a compound which has the reactive functional group is not particularly limited. It is possible to use a method in which a solution including a compound which has the reactive functional group is applied to the base member. As the applying method, it is possible to apply a method in the related art such as dip coating (dipping method), spraying, spin coating, dripping, doctor blading, brushing, roll coating, air knife coating, curtain coating, wire bar coating, gravure coating, mixed solution-impregnated sponge coating, and the like. In addition, concentration of a compound which has the reactive functional group in the applying solution is not particularly limited; for example, the compound which has the reactive functional group exists as much as an amount enough to be covalently bonded to the maleic acid polymer substance in a sufficient amount at the following Step (2). In consideration of reactivity with respect to the maleic acid polymer substance in a sufficient amount, a coating amount of the maleic acid polymer substance, and the like at the following Step (2), it is exemplary that the concentration of the compound which has the reactive functional group in the applying solution ranges from 0.5 weight % to 10 weight %, and it is exemplary to range from 2 weight % to 5 weight %.

A solvent for preparing the applying solution is not particularly limited; for example, the compound having the reactive functional group can be dissolved therein. The solvent can be suitably selected depending on the type of the compound having the reactive functional group to be used. For example, it is possible to exemplify a ketone-based solvent such as acetone, methyl ethyl ketone, methyl isobutyl ketone, cyclohexanone, and the like; an ester-based solvent such as butyl acetate, ethyl acetate, carbitol acetate, butyl carbitol acetate, and the like; an ether-based solvent such as methyl cellosolve, ethyl cellosolve, butyl ether, tetrahydrofuran, and the like; an alkane solvent such as butane, hexane, and the like; an aromatic-based solvent such as benzene, toluene, xylene, and the like; a halogen-based solvent such as dichloroethane, chloroform, methylene chloride, and the like; an alcohol-based solvent such as methanol, ethanol, isopropanol, ethylene glycol, and the like; and the like. One type of the above-described solvents may be independently used, or two types or more thereof may be used together. When the base member is made from a polymer material (a resin), or when a layer formed from a polymer material (the surface layer of the base member) is formed on the surface of the base member in advance (will be described later in detail), the above-described solvent causes thereof to be dissolved or to swell, thereby improving adhesion strength of the coating layer. Thus, lubricity (under normal conditions and severe conditions) can be retained for a longer period.

The applying solution may include a different additive other than the compound having the reactive functional group. A different additive is not particularly limited. For example, it is possible to exemplify a polymer material, a drug, and the like. As the polymer material, a polymer material which has been exemplified as the material constituting or forming the above-described base member can be similarly exemplified. Among those above, in consideration of easiness of forming the ground layer, and the like, it is exemplary to use polyvinyl chloride, a polyurethane resin, a polyamide resin, and a polyester resin. In addition, a drug can be suitably selected depending on the indwelling site of the medical device, the disease to which the drug is applied, and the like. Concentration of the different additive in the applying solution is not particularly limited. However, in consideration of easiness of forming the ground layer, and the like, it is exemplary that the concentration ranges from 0.5 weight % to 15 weight %, and it is exemplary to range from 2 weight % to 10 weight %.

The conditions of treating of the base member with the applying solution are not particularly limited; for example, the reactive functional group can be introduced to the desired surface of the base member under the conditions thereof. For example, it is exemplary that the applying solution is applied to the base member at a temperature ranging from 0° C. to 50° C. for a period ranging from one second to 48 hours.

When a metal material, glass, ceramic, and the like are used as the base member, before forming the ground layer, it is exemplary that a layer formed from a polymer material (the surface layer of the base member) is formed on the surface of the base member in advance. Accordingly, the base member and the ground layer can adhere to each other more firmly, and thus, adhesion strength of the coating layer can be improved. The type of a polymer material is not particularly limited. The type thereof can be suitably selected depending on the type of the base member. For example, as the polymer material, a polymer material which has been exemplified as the material constituting or forming the above-described base member can be similarly exemplified. Among those above, in consideration of a lubricity sustaining effect, adhesion with respect to the ground layer, and the like, it is exemplary to use polyvinyl chloride, a polyurethane resin, a polyamide resin, and a polyester resin. The thickness of a layer formed from a polymer material when the layer formed from a polymer material is formed on the surface of the base member in advance is not particularly limited. In consideration of the lubricity sustaining effect, adhesion with respect to the ground layer, and the like, it is exemplary that the thickness thereof ranges from 1 µm to 70 µm, and it is more exemplary to range from 5 µm to 50 µm.

After the applying solution is applied to the base member in the above-described manner, a coating film is dried and the ground layer is formed on the base member. The drying conditions are not particularly limited; for example, the ground layer can be formed under the drying conditions thereof. For example, it is exemplary that the drying temperature ranges approximately from room temperature (25° C.) to 80° C. In addition, it is exemplary that the drying time ranges approximately from five minutes to 48 hours.

2. Step (2)

In this Step, the base member (the base member/the ground layer) having the ground layer obtained through the above-described Step (1) is treated with the maleic acid polymer substance, to covalently bond the reactive functional group and the maleic acid polymer substance to each other and to form the resin coating layer which includes the maleic acid polymer substance, on the ground layer.

The method of treating the base member/the ground layer with the maleic acid polymer substance is not particularly limited. It is possible to use a method in which a solution (a coating layer forming solution) including the maleic acid polymer substance is applied to the base member. As the applying method, it is possible to apply a method in the related art such as dip coating (dipping method), spraying, spin coating, dripping, doctor blading, brushing, roll coating, air knife coating, curtain coating, wire bar coating, gravure coating, mixed solution-impregnated sponge coating, and the like. In addition, concentration of the maleic acid polymer substance in the coating layer forming solution is not particularly limited; for example, the concentration allows the coating layer to be formed using a sufficient amount of the maleic acid polymer substance. In consideration of a coating amount of the maleic acid polymer substance, and the like, it is exemplary that the concentration of the maleic acid polymer substance in the coating layer forming solution ranges from 0.1 weight % to 15 weight %, for example, from 0.5 weight % to 10 weight %. In such concentration, the medical device (the coating layer) can exhibit excellent lubricity at the time of wetting under normal conditions, lubricity at the time of wetting under severe conditions, and retainability of the lubricity thereof.

A solvent for preparing the coating layer forming solution is not particularly limited; for example, the maleic acid polymer substance can be dissolved therein. The solvent can be suitably selected depending on the type of the maleic acid polymer substance to be used. For example, it is possible to use a solvent similar to the solvent disclosed in the above-described Step (1). Among those above, it is exemplary to use methyl ethyl ketone, tetrahydrofuran (THF), acetone, and the like. The solvents seldom react or do not react to the reactive functional group which exists in the base member/the ground layer. In addition, the solvents have suitable solubility and swelling characteristics with respect to the base member/the ground layer. One type of the above-described solvents may be independently used, or two types or more thereof may be used together.

The coating layer forming solution may include a different additive other than the maleic acid polymer substance. A different additive is not particularly limited. For example, it is possible to exemplify a polymer material, a drug, and the like. As the polymer material, a polymer material which has been exemplified as the material constituting or forming the above-described base member can be similarly exemplified. In addition, a drug can be suitably selected depending on the indwelling site of the medical device, the disease to which the drug is applied, and the like. Concentration of the different additive in the coating layer forming solution is not particularly limited. In consideration of easiness of forming the coating layer, and the like, it is exemplary that the concentration ranges from 0.5 weight % to 15 weight %, for example, from 2 weight % to 10 weight %.

The conditions of treating the base member/the ground layer with the coating layer forming solution are not particularly limited; for example, an appropriate amount of the coating layer of the maleic acid polymer substance can be formed on the base member/the ground layer under the conditions. For example, it is exemplary that the coating layer forming solution is applied to the base member/the ground layer at a temperature ranging from 0° C. to 80° C. for a period ranging from one second to 48 hours, and it is exemplary to apply the coating layer forming solution at a temperature ranging from 10° C. to 30° C. for a period ranging from one second to one hour.

After the coating layer forming solution is applied to the base member/the ground layer in the above-described manner, the coating film is dried and the coating layer is formed on the base member/the ground layer. The drying conditions are not particularly limited; for example, the coating layer can be formed under the drying conditions thereof. For example, it is exemplary that the drying temperature ranges approximately from room temperature (25° C.) to 80° C. In addition, it is exemplary that the drying time ranges approximately from five minutes to 48 hours.

3. Step (3)

In this Step, alkali treatment of the base member having the ground layer and the resin coating layer obtained through the above-described Step (2) is performed. It is exemplary that the alkali treatment is performed by dipping the base member having the ground layer and the resin coating layer in the alkaline solution of which pH is equal to or greater than 9.5 at a temperature ranging from 25° C. to 70° C. for a period ranging from 0.1 hours to 20 hours. As such alkali treatment is performed, a carboxyl group (—COOH) and an ester portion (—COOR) in the maleic acid polymer substance in the coating layer is transformed into carboxylate (—COOX) in accordance with the below-described reaction, and the proportion of carboxylate (the peak height) is adjusted to range from 1.2 to 1.7. In the below-described reaction formula, the substituted groups "R" and "R'" are respectively defined to be similar to the substituted group "R" in the above-described Chemical Formula (a) and the substituted group "R'" in the above-described Chemical Formula (b). In addition, the below-described reaction formula, the substituted group "X" represents an alkali metal or an alkali earth metal. As the alkali metal, for example, there are lithium, sodium, potassium, rubidium, and cesium. In addition, as the alkali earth metal, for example, there are magnesium, calcium, strontium, and barium. It is exemplary that X is sodium, potassium, magnesium, and calcium; it is exemplary to be sodium and calcium; and it is exemplary to be sodium. In a case where X is sodium, when the maleic acid polymer substance comes into contact with a body fluid or blood, a sodium salt of a carboxyl group in the maleic acid polymer substance is caused to easily swell due to a body fluid or blood and is gelated, and thus, it is possible to exhibit particularly excellent lubricity.

[Chemical Formula 3]

In the above-described alkali treatment, the carboxyl group (—COOH) quickly turns into a form of a salt (—COOX). However, the ester portion (—COOR) does not turn into a form of the salt (—COOX) unless being under considerably strong alkali conditions (for example, high pH, a high processing temperature, and a long processing time). Therefore, when the alkali treatment time is short as shown in the below-described Comparison Example 1, for example, only the carboxyl group (—COOH) turns into a form of the salt (—COOX), that is, the peak height is only 1.1.

In the above-described alkali treatment, alkali used for preparing the alkaline solution is not particularly limited. It is possible to exemplify sodium hydroxide, potassium hydroxide, sodium carbonate, potassium carbonate, calcium hydroxide, sodium hydrogen carbonate, potassium hydrogen carbonate, lithium hydroxide, sodium, ammonium, and the like. Among those above, in consideration of pH of the alkaline solution, it is exemplary to use sodium hydroxide, potassium hydroxide, sodium carbonate, and calcium hydroxide, it is exemplary to use sodium hydroxide, sodium carbonate, calcium hydroxide, and it is exemplary to use sodium hydroxide. One type of the above-described alkali may be independently used, or two types or more thereof may be used together.

In addition, a solvent for dissolving the above-described alkali is not particularly limited. It is possible to exemplify water; alcohols such as methanol, ethanol, isopropanol, ethylene glycol, and the like; ethers such as tetrahydrofuran, butyl ether, and the like; aromatics such as benzene, toluene, and the like; amides such as N,N-dimethylformamide (DMF), and the like; and the like. Among those above, it is exemplary to use water. It is exemplary that the alkaline solution of which pH is equal to or greater than 9.5 is aqueous sodium hydroxide. One type of the above-described solvents may be independently used, or two types or more thereof may be used together.

It is exemplary that pH of the alkaline solution is equal to or greater than 9.5 (upper limit: 14). When pH of the alkaline solution is less than 9.5, the carboxyl group (—COOH) turns into a form of the salt (—COOX). However, the ester portion (—COOR) in a sufficient amount does not turn into the salt (—COOX), thereby leading to a high possibility in which the peak height cannot be caused to be equal to or greater than 1.2 (refer to the below-described Comparison Example 3). In consideration of easiness of adjusting the peak height, the time, and the like, it is exemplary that pH of the alkaline solution ranges from 10 to 13.5, and it is exemplary to range from 12 to 13.

The alkaline solution may include a different component other than alkali. As the different component, it is possible to exemplify sodium chloride, sodium bromide, potassium chloride, potassium bromide, lithium chloride, lithium bromide, ice, sucrose, and the like. It is exemplary to use sodium chloride. Favorable concentration of the different component is not particularly limited. However, it is exemplary to have the amount so as to obtain the concentration ranging from 0.01 millimol/L to 500 millimol/L in the alkaline solution.

In addition, it is exemplary that the dipping temperature of the base member having the ground layer and the resin coating layer in the alkaline solution ranges from 25° C. to 70° C. The dipping temperature denotes a temperature of the alkaline solution. For example, when the dipping temperature is less than 25° C., the carboxyl group (—COOH) turns into a form of the salt (—COOX). For example, the ester portion (—COOR) in a sufficient amount does not turn into the salt (—COOX), thereby leading to a high possibility in which the peak height cannot be caused to be equal to or greater than 1.2 (refer to the below-described Comparison Example 1). For example, when the dipping temperature exceeds 70° C., it is difficult to adjust the peak height. In consideration of easiness of adjusting the peak height, the time, and the like, it is exemplary that the dipping temperature ranges from 30° C. to 65° C., and it is exemplary to range from 40° C. to 60° C.

It is exemplary that the dipping time of the base member having the ground layer and the resin coating layer in the alkaline solution ranges from 0.1 hours to 20 hours. For example, when the dipping time is less than 0.1 hours, the carboxyl group (—COOH) turns into a form of the salt (—COOX). For example, the ester portion (—COOR) in a sufficient amount does not turn into the salt (—COOX), thereby leading to a high possibility in which the peak height cannot be caused to be equal to or greater than 1.2 (refer to the below-described Comparison Example 1). For example, when the dipping time exceeds 20 hours, there is the possibility that a resin coating film layer peels off (refer to the below-described Comparison Example 2). In consideration of easiness of adjusting the peak height, easiness of mass production, and the like, it is exemplary that the dipping time ranges from 0.5 hours to 14 hours, and it is exemplary to range from one hour to 14 hours.

After the above-described alkali treatment, a cleaning step may be performed as desired. By performing the cleaning step, transformation from the carboxyl group (—COOH) and the ester portion (—COOR) to the salt (—COOX) through alkali treatment can be easily completed. Therefore, a desired peak height can be realized and retained. Cleaning conditions are not particularly limited. For example, as cleaning liquid which can be used in the cleaning step, it is possible to exemplify water; alcohols such as methanol, ethanol, isopropanol, ethylene glycol, and the like; ketones such as acetone, methyl ethyl ketone, and the like; esters such as ethyl acetate and the like; halides such as chloroform and the like; alkanes such as butane, hexane, and the like; ethers such as tetrahydrofuran, butyl ether, and the like; aromatics such as benzene, toluene, and the like; amides such as N,N-dimethylformamide (DMF), and the like; and the like. One type of the above-described cleaning liquid may be independently used, or two types or more thereof may be used together. Among those above, it is exemplary to use water.

It is exemplary that the cleaning liquid does not include impurities, for example, does not include calcium. When there exists calcium, there is a case where a salt (for example, sodium) is partially substituted by calcium during the cleaning step so that the form thereof becomes unstable. Therefore, by cleaning the base member after alkali treatment with such cleaning liquid which does not include impurities (for example, calcium), it is possible to more effectively suppress and prevent swelling characteristics, for example, swelling characteristics under severe conditions from deteriorating. It is exemplary as the concentration of calcium in the cleaning liquid becomes lower. For example, it is exemplary that the concentration of calcium (Ca conversion) in the cleaning liquid is less than 20 mg/L (lower limit: 0 mg/L). It is exemplary that the base member after alkali treatment is cleaned with cleaning liquid in which the concentration of calcium (Ca conversion) is less than 20 mg/L. It is exemplary that the concentration of calcium (Ca conversion) in the cleaning liquid ranges from 0 mg/L to 10 mg/L. By cleaning the base member after alkali treatment with such cleaning liquid having the low concentration of calcium, it is possible to more effectively suppress and prevent swelling characteristics, for example, swelling characteristics and surface lubricity under severe conditions from deteriorating. When the cleaning method is also performed with respect to the resin coating layer that includes the maleic acid polymer substance having the peak height ratio is 1.1, it is possible to effectively suppress and prevent swelling characteristics, for example, swelling characteristics and surface lubricity under severe conditions from deteriorating.

The concentration of calcium (Ca conversion) in the cleaning liquid can be measured through a suitable method. In this description, the concentration of calcium (Ca conversion) in the cleaning liquid denotes a value measured by using a high-frequency inductively coupled plasma emission spectrometric analyzer (manufactured by Shimadzu Corporation, ICP emission spectrometric analyzer ICPS-8000).

Such cleaning liquid having the low concentration of calcium is not particularly limited. It is possible to exemplify distilled water, deionized water, reverse osmosis (RO) water, pure water, ultra-pure water, soft water, and the like.

In addition, it is exemplary that the cleaning temperature ranges from 0° C. to 70° C., and it is exemplary to range from 20° C. to 65° C. It is exemplary that the cleaning time ranges from 0.1 minutes to 120 minutes, and it is exemplary to range from 0.5 minutes to 30 minutes. Under such conditions, the alkaline solution can be sufficiently removed. Therefore, it is possible to realize and retain a desired peak height.

After the alkali treatment or the cleaning step described above, the alkali treatment or the cleaning step described above may be performed again as desired, thereby performing transformation into carboxylate and adjustment of the peak height. In addition, before the alkali treatment or the cleaning step described above is performed again, cleaning may be performed with an acid aqueous solution such as hydrochloric, sulfuric, citric acid, and the like as desired.

After the alkali treatment or the cleaning step, the base member having the ground layer and the resin coating layer is dried as desired. The drying conditions are not particularly limited; for example, the base member, the ground layer, and the resin coating layer after the alkali treatment or the cleaning step can be sufficiently dried under the conditions thereof. For example, it is exemplary that the drying temperature ranges approximately from room temperature (25° C.) to 80° C. In addition, it is exemplary that the drying temperature ranges approximately from five minutes to 48 hours.

In the medical device which is obtained as described above, the maleic acid polymer substance having the peak height ratio ranging from 1.2 to 1.7 is covalently bonded to the reactive functional group, and thus, the coating layer is formed on the surface of the base member which is inserted into a living body. Meanwhile, in the medical device according to the present disclosure, the portion which is not inserted into a living body may be subjected to non-lubrication processing. The non-lubrication processing is not particularly limited. For example, a method disclosed in JP-A-4-144567 in which an isocyanate compound is used can be used. It is considered that the isocyanate compound causes non-lubrication thereof by performing grafting with respect to the maleic acid polymer substance and performing partial cross-linking thereof.

The medical device which is obtained as described above has a sufficient amount of carboxylate (a metal salt of a carboxyl group). For example, even when a portion of a metal salt of a carboxyl group is transformed into a carboxyl group (—COOH) under severe conditions (for example, conditions of high humidity), a sufficient amount of carboxylate (a metal salt of a carboxyl group) remains in the coating layer. For this reason, even when being under severe conditions such as high temperature, low temperature, high humidity, and the like, the coating layer according to the present disclosure can retain and exhibit excellent lubricity without deteriorating the lubricity at the time of wetting. Accordingly, the medical device according to the present disclosure can retain and exhibit excellent lubricity even when being influenced by a severe environment and the like occurring at the time of transportation or in a country where the medical device is used.

Exemplary effects of the present disclosure will be described using the following Examples and Comparison Examples. However, the technical scope of the present disclosure is not limited to only the following Examples. In the below-described Examples, unless otherwise specified, operations are performed at room temperature (25° C.).

Example 1

A Ni—Ti alloy-made wire having the outer diameter of 0.25 mm was coated with a thermoplastic polyurethane resin, thereby having the outer diameter of 0.3 mm. Subsequently, the wire coated with the polyurethane resin was dipped in a tetrahydrofuran (THF) solution of polyvinyl chloride (PVC) and 4,4'-diphenylmethane diisocyanate (MDI) (each concentration=5 weight %) at room temperature (25° C.) for one second and was dried at room temperature (25° C.) for 30 minutes.

The wire was dipped in a THF solution having 1 weight % of half ethyl ester (degree of esterification=approximately 50%) of a methyl vinyl ether maleic anhydride copolymer (brand name: GANTREZ AN-169, manufactured by G.A.F., the weight-average molecular weight=$1.98 \times 10^6$) at room temperature (25° C.) for one second, and was dried at approximately 60° C. for 12 hours, thereby obtaining an untreated product of a guide wire. The half ethyl ester (degree of esterification=approximately 50%) of a methyl vinyl ether maleic anhydride copolymer used in the present Example was constituted by a maleic acid of 50 mol %, a constituting unit derived from ester thereof, and a constituting unit derived from methyl vinyl ether of 50 mol %. The half ethyl ester was constituted by the below-described constituting units.

[Chemical Formula 4]

The untreated product of a guide wire which has been obtained in such a manner was dipped for 2 hours in an aqueous sodium hydroxide (pH=13) of 0.1 mol/L heated to approximately 50° C. Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a medical device (1). The measured peak height ratio (the IR ratio) of the medical device (1) which has been obtained in such a manner was 1.2.

Example 2

Similar to Example 1, an untreated product of a guide wire was obtained.

Subsequently, the untreated product of a guide wire which has been obtained in such a manner was dipped for 4 hours in an aqueous sodium hydroxide of 0.1 mol/L heated to approximately 50° C. Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a medical device (2). The measured peak height ratio (the IR ratio) of the medical device (2) which has been obtained in such a manner was 1.4.

Example 3

Similar to Example 1, an untreated product of a guide wire was obtained.

Subsequently, the untreated product of a guide wire which has been obtained in such a manner was dipped for 6 hours in an aqueous sodium hydroxide of 0.1 mol/L heated to approximately 50° C. Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a medical device (3). The measured peak height ratio (the IR ratio) of the medical device (3) which has been obtained in such a manner was 1.5.

Example 4

Similar to Example 1, an untreated product of a guide wire was obtained.

Subsequently, the untreated product of a guide wire which has been obtained in such a manner was dipped for 14 hours in an aqueous sodium hydroxide of 0.1 mol/L heated to approximately 50° C. Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a medical device (4). The measured peak height ratio (the IR ratio) of the medical device (4) which has been obtained in such a manner was 1.7.

Example 5

Similar to Example 1, an untreated product of a guide wire was obtained.

Subsequently, the untreated product of a guide wire which has been obtained in such a manner was dipped for 2 hours in a sodium carbonate aqueous solution (pH=10.5) of 1.2 mmol/L heated to approximately 50° C. Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a medical device (5). The measured peak height ratio (the IR ratio) of the medical device (5) which has been obtained in such a manner was 1.3.

Example 6

Similar to Example 1, an untreated product of a guide wire was obtained.

Subsequently, the untreated product of a guide wire which has been obtained in such a manner was dipped for 2 hours in a sodium carbonate aqueous solution (pH=10.5) of 1.2 mmol/L in which sodium chloride (51.3 mmol/L) heated to approximately 50° C. was added. Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a medical device (6). The measured peak height ratio (the IR ratio) of the medical device (6) which has been obtained in such a manner was 1.3.

Example 7

Similar to Example 1, an untreated product of a guide wire was obtained.

Subsequently, the untreated product of a guide wire which has been obtained in such a manner was dipped for 1 hours in an aqueous calcium hydroxide (pH=12.3) of 0.01 mol/L heated to approximately 50° C. Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a medical device (7). The measured peak height ratio (the IR ratio) of the medical device (7) which has been obtained in such a manner was 1.4.

Example 8

Similar to Example 1, an untreated product of a guide wire was obtained.

Subsequently, the untreated product of a guide wire which has been obtained in such a manner was dipped for 2 hours in an aqueous sodium hydrogen carbonate (pH=9.5) of 35 mmol/L in which sodium chloride (15 mmol/L) heated to approximately 50° C. was added. Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a medical device (8). The measured peak height ratio (the IR ratio) of the medical device (8) which has been obtained in such a manner was 1.3.

Example 9

Similar to Example 1, an untreated product of a guide wire was obtained.

The untreated product of a guide wire which has been obtained in such a manner was dipped for 2 hours in an aqueous sodium hydroxide (pH=13) of 0.1 mol/L heated to approximately 50° C. Subsequently, the untreated product of a guide wire was cleaned for two hours with tap water (the concentration of calcium: 30 mg/L) heated to approximately 60° C., and was dried at room temperature (25° C.) for 24 hours, thereby obtaining a medical device (9). The measured peak height ratio (the IR ratio) of the medical device (9) which has been obtained in such a manner was 1.2.

Comparison Example 1

Similar to Example 1, an untreated product of a guide wire was obtained.

Subsequently, the untreated product of a guide wire which has been obtained in such a manner was dipped for one minute in an aqueous sodium hydroxide (pH=13) of 0.1 mol/L at room temperature (25° C.). Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a comparison medical device (1). The measured peak height ratio (the IR ratio) of the comparison medical device (1) which has been obtained in such a manner was 1.1.

Comparison Example 2

Similar to Example 1, an untreated product of a guide wire was obtained.

Subsequently, when the untreated product of a guide wire which has been obtained in such a manner was dipped for 24 hours in an aqueous sodium hydroxide of 0.1 mol/L heated to approximately 50° C., the resin coating layer peeled off (a comparison medical device (2)). Therefore, the peak height ratio (the IR ratio) of the coating layer of the comparison medical device (2) could not be measured.

Comparison Example 3

Similar to Example 1, an untreated product of a guide wire was obtained.

Subsequently, the untreated product of a guide wire which has been obtained in such a manner was dipped for 4 hours in a solution (pH=8.2) which is obtained by dissolving NaCl of 0.1 weight % and $NaHCO_3$ of 0.05 weight % in hot water at approximately 60° C. Subsequently, the untreated product of a guide wire was cleaned with hot water (the concentration of calcium: 30 mg/L) at 60° C. for one minute, and was dried at room temperature (25° C.) for 24 hours, thereby obtaining a comparison medical device (3). The measured peak height ratio (the IR ratio) of the comparison medical device (3) which has been obtained in such a manner was 1.1.

Comparison Example 4

Similar to Example 1, an untreated product of a guide wire was obtained.

Subsequently, the untreated product of a guide wire which has been obtained in such a manner was dipped for one minute in an aqueous sodium hydroxide (pH=12.3) of 0.01 mol/L at room temperature (25° C.). Subsequently, the untreated product of a guide wire was cleaned with distilled water (the concentration of calcium: 0 mg/L) at room temperature (25° C.) for one minute, and was dried at room temperature (25° C.) for 24 hours, thereby obtaining a comparison medical device (4). The measured peak height ratio (the IR ratio) of the comparison medical device (4) which has been obtained in such a manner was 1.1.

The below-described test was performed for the medical devices (1) to (8) manufactured in Examples 1 to 8 and the comparison medical devices (1) to (3) manufactured in Comparison Examples 1 to 3, thereby evaluating swelling characteristics under a normal environment, and swelling characteristics and surface lubricity under severe conditions. The results are indicated in the below-described Table 2.
(Evaluation of Swelling Characteristics Under Normal Environment)

Each of the medical devices is dipped in distilled water at the temperature of 25° C. for one minute, and the film thickness (μm) is measured by using a microscope after being sufficiently subjected to swelling. In accordance with the measured film thickness, classification is performed as follows. When the film thickness is equal to or greater than 20 μm ("O" in the below-described Tables 2 and 3), it is determined that the medical device thereof can exhibit sufficient lubricity. In addition, when the film thickness is equal to or greater than 10 μm ("O" and "Δ" in the below-described Tables 2 and 3), it is determined that the medical device thereof can be acceptable in the point of lubricity.
O: The film thickness after being subjected to swelling is equal to or greater than 20 μm.
Δ: The film thickness after being subjected to swelling ranges from 10 μm to 20 μm.
X: The film thickness after being subjected to swelling is less than 10 μm.
(Evaluation of Swelling Characteristics Under Severe Conditions)

Each of the medical devices is subjected to the hygrothermal cycle test under the conditions indicated in the below-described Table 1. Each of the medical devices after the hygrothermal cycle test is dipped in distilled water at the temperature of 25° C. for one minute, and after being sufficiently subjected to swelling, the film thickness (μm) is measured by using a microscope. In accordance with the measured film thickness, classification is performed similarly to that described above (evaluation of swelling characteristics under a normal environment). When the film thickness is equal to or greater than 20 μm ("O" in the below-described Tables 2 and 3), it is determined that the medical device thereof can exhibit sufficient lubricity. In addition, when the film thickness is equal to or greater than 10 μm ("O" and "Δ" in the below-described Tables 2 and 3), it is determined that the medical device thereof can be acceptable in the point of lubricity.

TABLE 1

Hygrothermal Cycle Test

| Step | Temperature (° C.) | Humidity (% RH) | Time (hrs) |
|---|---|---|---|
| 1 | 65 | 95 | 5.5 |
| 2 | 25 | 65 | 5.0 |
| 3 | 65 | 95 | 5.5 |
| 4 | 25 | 65 | 2.0 |
| 5 | −10 | — | 4.0 |
| 6 | 25 | 65 | 2.0 | environment, it is learned that the film thickness indicates acceptable lubricity. In contrast, the comparison medical devices (1) and (3) in Comparison Examples 1 and 3 of which the peak height ratios (the IR ratios) are less than 1.2 have the film thickness at the time of swelling equal to or greater than 20 μm under a normal environment (at room temperature), thereby indicating favorable lubricity. However, under severe conditions (after the hygrothermal cycle test), the film thickness at the time of swelling becomes less than 10 μm, and thus, it is learned that lubricity is beyond the permissible range. Both of the peak height ratios of the medical device (2) in Example 2 and the medical device (7) in Example 7 are 1.4. However, the medical device (2) in Example 2 having the resin coating layer that includes the maleic acid polymer substance in a form of a sodium salt exhibits more excellent swelling characteristics in both cases under a normal environment and under severe conditions compared to the medical device (7) in Example 7 having the resin coating layer that includes the maleic acid polymer substance in a form of a calcium salt. According to the result thereof, in addition to the peak height ratio of the maleic acid polymer substance included in the resin coating layer, it is considered that the form of a salt also plays an important role in regard to swelling characteristics. It is considered that the maleic acid polymer substance in a form of a sodium salt is caused to more efficiently swell and is gelated when coming into contact with a body fluid or blood and can exhibit more excellent lubricity.

TABLE 2

| | Processing Conditions | | Peak Height Ratio | Swelling Characteristics under Normal Environment | Swelling Characteristics under Severe Conditions |
|---|---|---|---|---|---|
| Example 1 | 0.1 mol/L NaOH | 50° C. 2 hrs | 1.2 | ○ | ○ |
| Example 2 | 0.1 mol/L NaOH | 50° C. 4 hrs | 1.4 | ○ | ○ |
| Example 3 | 0.1 mol/L NaOH | 50° C. 6 hrs | 1.5 | ○ | ○ |
| Example 4 | 0.1 mol/L NaOH | 50° C. 14 hrs | 1.7 | ○ | ○ |
| Example 5 | 1.2 mmol/L Na$_2$CO$_3$ | 50° C. 2 hrs | 1.3 | ○ | ○ |
| Example 6 | 1.2 mmol/L Na$_2$CO$_3$ 51.3 mmol/L NaCl | 50° C. 2 hrs | 1.3 | ○ | ○ |
| Example 7 | 0.01 mol/L Ca(OH)$_2$ | 50° C. 1 hr | 1.4 | ○ | Δ |
| Example 8 | 35 mmol/L NaHCO$_3$ 15 mmol/L Na$_2$CO$_3$ | 50° C. 2 hrs | 1.3 | ○ | ○ |
| Comparison Example 1 | 0.1 mol/L NaOH | r.t. 1 min | 1.1 | ○ | X |
| Comparison Example 2 | 0.1 mol/L NaOH | 50° C. 24 hrs | | peeled off | |
| Comparison Example 3 | 0.05 wt % NaHCO$_3$ 0.1 wt % NaCl | 60° C. 4 hrs | 1.1 | ○ | X |

According to Table 2, it is learned that the medical devices (1) to (6), and (8) in Examples 1 to 6, and 8 of which the peak height ratios (the IR ratios) are equal to or greater than 1.2 have the film thickness at the time of swelling equal to or greater than 20 μm in both cases under a normal environment (at room temperature) and under severe conditions (after the hygrothermal cycle test), thereby indicating favorable lubricity. In addition, the medical instrument (7) in Example 7 of which the peak height ratio (the IR ratio) is equal to or greater than 1.2 has the film thickness at the time of swelling equal to or greater than 20 μm under a normal environment (at room temperature), thereby indicating favorable lubricity. Meanwhile, under severe conditions (after the hygrothermal cycle test), the film thickness at the time of swelling ranges from 10 μm to less than 20 μm, and lubricity thereof is slightly deteriorated. However, in both cases under a normal environment and under a severe (Evaluation of Surface Lubricity)

Figure 1:
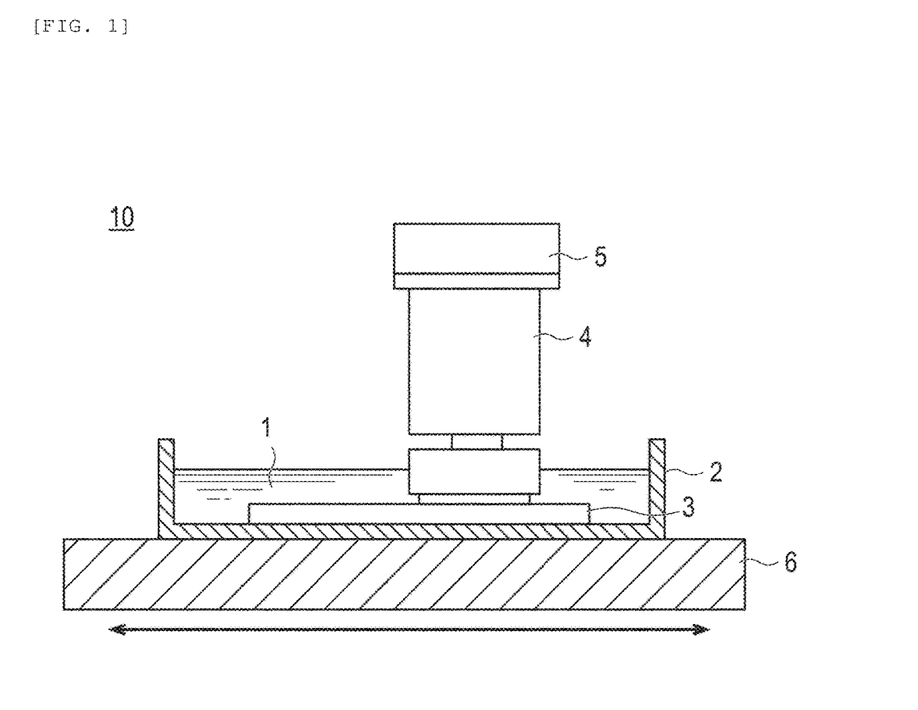
FIG. 1 is a schematic view of a surface lubricity evaluation test device (friction tester).

Regarding each of the medical devices (hereinafter, also referred to as "sample") subjected to the hygrothermal cycle test, lubricity of the surface lubrication layer is evaluated in accordance with the below-described method by using the friction tester (manufactured by Trinity Laboratories Inc., Handy Tribo Master TL201) 10 illustrated in FIG. 1.

Each of the above-described samples 3 after the hygrothermal cycle test is fixed to a petri dish 2 and is dipped in the water 1 having a depth enough to allow the sample 3 to be soaked in its entirety. The petri dish 2 is mounted in a moving table 6 of the friction tester 10 illustrated in FIG. 1. A columnar butyl rubber terminal (φ=7 mm) 4 is brought into contact with the sample 3, and a load 5 of 70 g is applied to the top of the terminal 4. Under the setting of the velocity of 10 m/sec, and the moving distance of 25 mm, the moving table 6 is caused to horizontally reciprocate five times, and the sliding resistance value (gf) on the fifth lap is recorded. The results are illustrated in FIG. 2.

Figure 2:
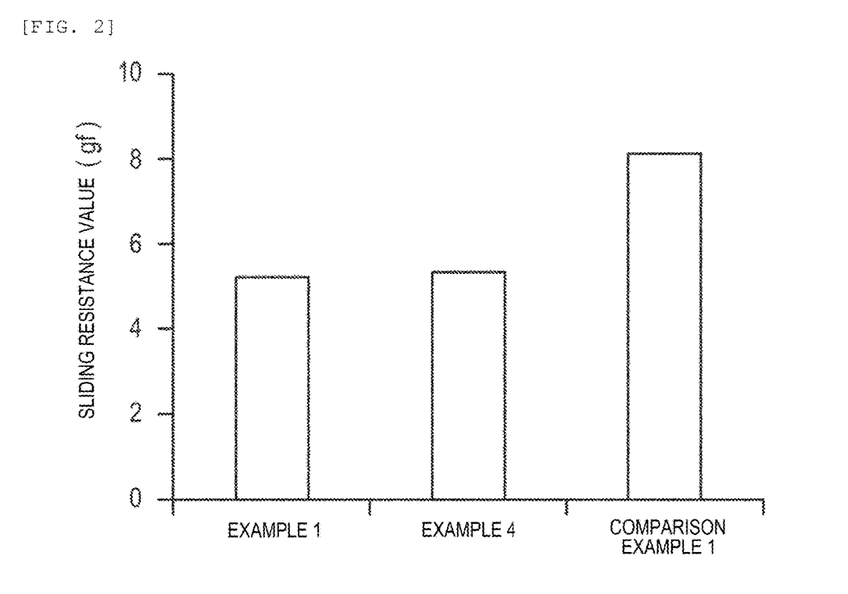
FIG. 2 is a graph illustrating an evaluation result of surface lubricity.

According to FIG. 2, in the medical device according to the present disclosure, it is considered that more excellent lubricity can be applied to the surface of the medical device under severe conditions (after the hygrothermal cycle test) compared to the technology in the related art. The medical devices (2), (3), (5), (6), and (8) in Example 2, 3, 5, 6, and 8 indicate the sliding resistance value equivalent to the medical device (1) in the below-described Example 1 (not illustrated).

Regarding the medical devices (1), (7), and (9) manufactured through Examples 1, 7 and 9 and the comparison medical device (4) manufactured through Comparison Example 4 described above, the peak height ratios are measured again after the hygrothermal cycle test under the conditions indicated in the above-referenced Table 1. The results thereof is indicated in the following Table 3 together with the results of swelling characteristics under a normal environment, and swelling characteristics and surface lubricity under severe conditions. In the space of surface lubricity in the following Table 3, "O" indicates a case where the sliding resistance value (gf) on the fifth lap is less than 6 gf, "Δ" indicates a case where the sliding resistance value (gf) on the fifth lap ranges from 6 gf to less than 8 gf, and "X" indicates a case where the sliding resistance value (gf) on the fifth lap is equal to or greater than 8 gf. In addition, in the above-described classification, in a case of O (the sliding resistance value (gf) on the fifth lap is less than 6 gf), it is determined that the medical device thereof can exhibit sufficient surface lubricity. In addition, in a case of A (the sliding resistance value (gf) on the fifth lap ranges from 6 gf to less than 8 gf), it is determined that the medical device thereof is acceptable in the point of surface lubricity.

becomes less than 10 μm, and thus, it is learned that lubricity is beyond the permissible range.

In addition, in Example 1 in which cleaning is performed with distilled water having low concentration of calcium after alkali treatment, it is learned that all the peak height ratio, swelling characteristics, and surface lubricity can be retained even after being under severe conditions (after the hygrothermal cycle test). In contrast, in Example 9 in which cleaning is performed with tap water having high concentration of calcium after alkali treatment, it is learned that the peak height ratio, swelling characteristics, and surface lubricity are deteriorated after being under severe conditions (after the hygrothermal cycle test). According to the results thereof, it is considered to be exemplary that cleaning after alkali treatment is performed with cleaning liquid having low concentration of calcium from the viewpoint of retaining the peak height ratio, swelling characteristics, and surface lubricity under severe conditions.

The detailed description above describes exemplary aspects of medical devices and methods associated with such medical devices. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device capable of being inserted into a living body, the medical device comprising:
a resin coating layer that includes a maleic acid polymer substance,

TABLE 3

| | Processing Conditions | | | Under Normal Environment | | | Under Severe Conditions | | |
|---|---|---|---|---|---|---|---|---|---|
| | | | | Peak Height Ratio | swelling characteristics | surface lubricity | Peak Height Ratio | swelling characteristics | surface lubricity |
| Example 1 | 0.1 mol/L NaOH | 50° C. 2 hrs | distilled water cleaning | 1.2 | ○ | ○ | 1.2 | ○ | ○ |
| Example 7 | 0.01 mol/L Ca(OH)$_2$ | 50° C. 1 hr | distilled water cleaning | 1.4 | ○ | Δ | 1.0 | Δ | Δ |
| Example 9 | 0.1 mol/L NaOH | 50° C. 2 hrs | tap water cleaning | 1.2 | ○ | ○ | 1.0 | Δ | Δ |
| Comparison Example 4 | 0.01 mol/L Ca(OH)$_2$ | r.t. 1 min | distilled water cleaning | 1.1 | ○ | ○ | 0.8 | x | x |

According to the above-described Table 3, it is learned that the medical devices (1), (7), and (9) in Examples 1, 7, and 9 of which the peak height ratios (the IR ratio) are equal to or greater than 1.2 have the film thickness at the time of swelling equal to or greater than 10 μm in both cases under a normal environment (at room temperature) and under severe conditions (after the hygrothermal cycle test), thereby indicating lubricity which is favorable or acceptable. In contrast, the comparison medical device (4) in Comparison Example 4 of which the peak height ratio (the IR ratio) is less than 1.2 have the film thickness at the time of swelling equal to or greater than 20 μm under a normal environment (at room temperature), thereby indicating favorable lubricity. However, under severe conditions (after the hygrothermal cycle test), the film thickness at the time of swelling wherein the resin coating layer is provided on a surface of a base member of the medical device, wherein the resin coating layer is formed by covalently bonding the maleic acid polymer substance to a reactive functional group which exists on at least the surface of the base member of the medical device, and wherein the maleic acid polymer substance has a ratio of a peak height of carboxylate with respect to a total peak height of carboxylic acid ester and a carboxylic acid in a range from 1.2 to 1.7 when being measured through infrared spectroscopy, and wherein the ratio of a peak height of carboxylate with respect to a total peak height of carboxylic acid ester and a carboxylic acid in the range from 1.2 to 1.7 when being measured through infrared spectroscopy is obtained by subjecting the maleic acid polymer substance to an alkali treatment, wherein the maleic acid polymer substance includes a constituting unit of formula (a'), a constituting unit of formula (a''), or a combination thereof:

wherein in formulas (a') and (a''), X represents an alkali metal or an alkaline earth metal, and R represents a straight chain or branched alkyl group of carbon atom numbers 1 to 24.

2. The medical device according to claim 1, wherein the reactive functional group is an isocyanate group, an amino group, an aldehyde group, or an epoxy group.

3. The medical device according to claim 1, wherein the maleic acid polymer substance is an alkyl vinyl ether-maleic acid ester copolymer.

4. The medical device according to claim 2, wherein the maleic acid polymer substance is an alkyl vinyl ether-maleic acid ester copolymer.

5. The medical device according to claim 1, wherein the maleic acid polymer substance has a ratio of a peak height of carboxylate with respect to a total peak height of carboxylic acid ester and a carboxylic acid in a range from 1.2 to 1.6 when being measured through infrared spectroscopy.

6. The medical device according to claim 1, wherein the maleic acid polymer substance has a ratio of a peak height of carboxylate with respect to a total peak height of carboxylic acid ester and a carboxylic acid in a range from 1.2 to 1.5 when being measured through infrared spectroscopy.

7. The medical device according to claim 1, wherein the resin coating layer is formed on at least a surface portion of the medical device which contacts a body fluid or blood.

8. The medical device according to claim 1, wherein the maleic acid polymer substance includes a constituting unit of formula (a), wherein in formula (a), R represents a straight chain or branched alkyl group of carbon atom numbers 1 to 24.

9. The medical device according to claim 1, wherein the maleic acid polymer substance includes the constituting unit of formula (a') and the constituting unit of formula (a'').

10. The medical device according to claim 1, wherein a weight-average molecular weight of the maleic acid polymer substance ranges from 10,000 to 7,000,000.

11. The medical device according to claim 1, wherein a weight-average molecular weight of the maleic acid polymer substance ranges from 100,000 to 5,000,000.

12. The medical device according to claim 1, wherein the reactive functional group includes a diazonium group, an azide group, an isocyanate group, an acid chloride group, an acid anhydride group, an imino carbonate ester group, an amino group, a carboxyl group, an epoxy group, a hydroxyl group, a peroxide group, an aldehyde group, or a combination thereof.

13. The medical device according to claim 1, wherein the reactive functional group includes an isocyanate group, an amino group, an aldehyde group, an epoxy group, or a combination thereof.

14. A method of manufacturing the medical device according to claim 1, the method comprising:
   treating a base member of the medical device with a solution including a compound which has a reactive functional group, to form a ground layer in which the reactive functional group exists, on at least a surface of the base member;
   treating the ground layer with a maleic acid polymer substance, to covalently bond the reactive functional group and the maleic acid polymer substance to each other and to form a resin coating layer which includes the maleic acid polymer substance, on the ground layer; and
   performing an alkali treatment of the base member on which the ground layer and the resin coating layer are formed,
   wherein the alkali treatment is performed by dipping the base member on which the ground layer and the resin coating layer are formed, in an alkaline solution having a pH of equal to or greater than 9.5 at a temperature ranging from 25° C. to 70° C. for a period ranging from 0.1 hours to 20 hours.

15. The method according to claim 14, further comprising:
   cleaning the base member after alkali treatment, with a cleaning liquid of which the concentration of calcium is less than 20 mg/L.

16. The method according to claim 15, wherein the concentration of calcium in the cleaning liquid ranges from 0 mg/L to 10 mg/L.

17. The method according to claim 14, wherein the alkaline solution having a pH of equal to or greater than 9.5 is aqueous sodium hydroxide.

18. The method according to claim 15, wherein the alkaline solution having a pH of equal to or greater than 9.5 is aqueous sodium hydroxide.

19. The medical device according to claim 1, wherein the alkali treatment comprises dipping the maleic acid polymer substance in an alkaline solution of which pH is equal to or greater than 9.5 at a temperature ranging from 25 to 70° C. for a period ranging from 0.1 to 20 hours.

20. The medical device according to claim 1, wherein X represents lithium, sodium, potassium, rubidium, cesium, magnesium, calcium, strontium, or barium.

* * * * *